United States Patent [19]

Russo et al.

[11] Patent Number: 5,227,083
[45] Date of Patent: Jul. 13, 1993

[54] POLYPROPYLENE OXIDE DIALKYLSARCOSINATES FOR USE AS RUST AND HAZE INHIBITING LUBRICATING OIL ADDITIVE

[75] Inventors: Joseph M. Russo, Poughkeepsie, N.Y.; Thomas F. DeRosa, Passaic, N.J.; Rodney L. Sung, Fishkill; Benjamin J. Kaufman, Hopewell Junction, both of N.Y.

[73] Assignee: Texaco Inc., White Plains, N.Y.

[21] Appl. No.: 842,688

[22] Filed: Feb. 27, 1992

[51] Int. Cl.$^5$ ................. C10M 145/38; C07C 229/08
[52] U.S. Cl. .......................... 252/51.5 R; 252/51.5 A; 252/54.6; 252/56 R; 252/52 A; 560/155; 554/35
[58] Field of Search ............ 252/51.5 R, 52 A; 560/155; 554/35

[56] References Cited

U.S. PATENT DOCUMENTS

| | | | |
|---|---|---|---|
| 3,652,410 | 3/1972 | Hollinghurst et al. | 252/32.7 E |
| 3,816,315 | 6/1974 | Morduchowitz et al. | 252/51.5 A |
| 4,198,306 | 4/1980 | Lewis | 252/51.5 R |
| 4,537,693 | 8/1985 | Campbell | 252/51.5 R |
| 4,557,848 | 12/1985 | Sung et al. | 252/51.5 R |
| 4,696,755 | 9/1987 | Campbell | 252/51.5 R |
| 4,758,247 | 7/1988 | Sung | 44/399 |
| 4,758,797 | 4/1988 | Halpern et al. | 252/51.5 R |
| 4,981,493 | 1/1991 | Sung | 44/331 |
| 5,131,921 | 7/1992 | Sung et al. | 44/389 |

OTHER PUBLICATIONS

Chemistry of Organic Compounds, 2nd ed., W. B. Saunders Co., 1951, p. 785.

*Primary Examiner*—Prince Willis, Jr.
*Assistant Examiner*—Alan D. Diamond
*Attorney, Agent, or Firm*—James J. O'Loughlin; Vincent A. Mallare

[57] ABSTRACT

A lubricating oil additive with rust and haze inhibiting properties which comprises the reaction product of an alkyl sarcosine represented by the figure

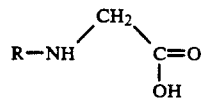

where R is a ($C_3$–$C_{30}$) alkyl radical and poly (propylene oxide). A lubricating oil composition containing the additive is also provided.

9 Claims, No Drawings

POLYPROPYLENE OXIDE DIALKYLSARCOSINATES FOR USE AS RUST AND HAZE INHIBITING LUBRICATING OIL ADDITIVE

BACKGROUND OF THE INVENTION

This invention relates to an additive which imparts haze-free rust inhibition to diesel lubricating oils, and to a diesel lubricating oil composition which contains such an additive. More specifically, this invention relates to a diesel lubricating oil additive which comprises the reaction product of an oligomeric alkoxide diol and an alkyl sarcosine, and to a diesel lubricating oil composition in which the additive of the present invention is dissolved.

As is well known to those skilled in the art, lubricating oils must be characterized by resistance to oxidation, and by rust and corrosion inhibition. It is also desirable from aesthetic perspective to have a haze-free product. The oils used as lubricants in the crankcases of large diesel engines, such as marine and railway diesel engines, are subject to uniquely harsh operating conditions and thus special attention must be directed to the severe problems which are encountered. These oils are therefore typically formulated to contain anti-wear additives, oxidation inhibitors, demulsifying agents, rust-inhibitors, etc.

Lubricants used in the crankcases of marine diesel engines are burdened by a severe rust protection requirement. The rust forms as the result of water coming into contact with ferrous metal engine parts. There are two water sources which are responsible: the first is water produced by the combustion of the diesel fuel; the second is seawater. Of the two, seawater is considerably more abundant and corrosive.

This is an old problem, and diesel lubricating oils have been formulated with additives to inhibit the formation of rust. However, the treatment of one problem, i.e., rust formation, has introduced another problem. The addition of rust inhibitors to lubricating oil compositions has been found to cause the formation of haze in the lubricating oil. The formation of haze is undesirable since it masks or interferes with the determination of the presence of undesirable components, including decomposition products, water, and solid particles in the lubricant.

In addition, consumers have come to equate product clarity or aesthetics with product superiority. In this context, hazy products would dramatically curtail product acceptance by consumers.

The advent of new, more fuel efficient railway diesel engines has put a greater demand on the oxidation resistance of railway diesel lubricants. Oxidized lubricants lead to increased corrosive attack of engine metal surfaces; consequently, lubricants employed in newer railway diesel engines must be changed more frequently to prevent such corrosive attack.

Thus, an object of the present invention, is to provide an additive which will impart rust inhibition to diesel lubricating oil compositions, but which does not cause haze to form.

Another object of this invention is to provide a diesel lubricant additive which will inhibit the formation of rust in a lubricating oil, but which will not cause undesirable haze to form. It is another object to provide a novel lubricant composition, suitable for use in large marine and railway diesel engines, characterized by its rust and haze resistance. It is still another object of this invention to provide a process for producing such a lubricating oil additive and a method for imparting rust resistance to a lubricating oil without causing haze to form. Other objects will be apparent to those skilled in the art.

SUMMARY OF THE INVENTION

The present invention provides: a diesel lubricating oil additive which imparts rust and haze inhibition to diesel lubricating oil compositions and diesel lubricating oil compositions containing such additives.

The present diesel lubricating oil additive comprises the reaction product of an alkyl sarcosine (I) represented by the general formula (I):

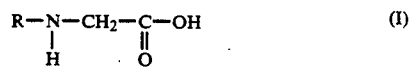

where R is a ($C_3$–$C_{30}$) alkyl radical optionally containing one or more heteroatoms; and poly(propylene oxide) (II) represented by the formula: (II)

where n varies from 1 to 5000

The diesel lubricating oil additive of the present invention is the addition product of the two aforementioned components (III):

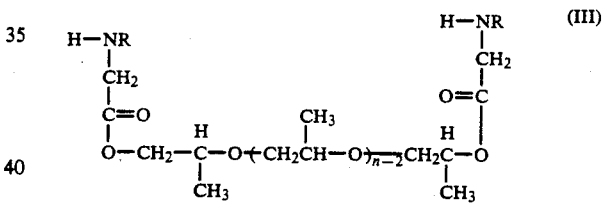

where n and R are as defined above.

The present invention also provides a diesel lubricating oil composition comprising a major portion of a hydrocarbon lubricating oil and a minor, effective portion of the additive composition described above, sufficient to impart rust inhibition and haze resistance to the diesel lubricating oil composition.

DETAILED DESCRIPTION OF THE INVENTION

The Alkyl Sarcosine Reactant

The alkyl sarcosine reactant is represented by the general formula:

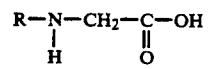

where R is a ($C_3$–$C_{30}$) alkyl radical; preferably R is a ($C_{10}$–$C_{30}$) alkyl radical. R may be aliphatic, cyclic or acyclic, branched in a systematic or random fashion or unbranched; aromatic-aliphatic; aliphatic-aromatic; aromatic with one or more substituents on the aromatic ring; or polyaromatic. Moreover, R also may contain one or more heteroatoms, e.g., nitrogen and oxygen.

The Poly (propylene oxide) Diol Reactant

The poly (propylene oxide) reactant useful in this invention is represented by the formula:

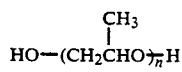

where n varies from 1 to 5000; and preferably n varies between 100 and 300 and most preferably n is 200.

Alkyl sarcosines are available under the tradenames HAMPOSYL C, —L, —S, and —T are manufactured and sold by W. R. Grace and Company of Nashua, N.H. Poly(Propylene oxide) is manufactured and sold by Texaco Chemical Company of Houston, Tex.

The additive of the present invention is produced by reacting an equivalent of the poly(propylene oxide) with two equivalents of an alkyl sarcosine according to the reaction depicted below in Equation 1 (EQ. 1) where R and n are as defined above.

EQ. 1:

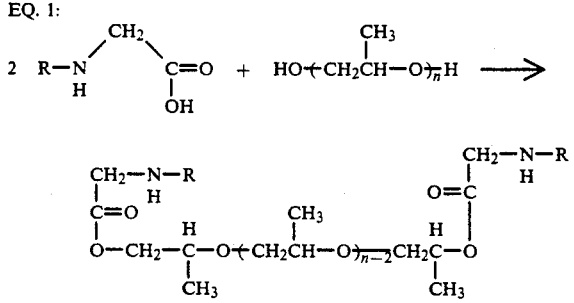

The following examples are provided to illustrate the synthesis of materials of this invention.

EXAMPLE 1

Preparation of Poly(propylene oxide)-di-(lauroyl sarcosinate)

A 1 liter 3-neck round bottom flask containing a reflux condensor, thermometer, magnetic stirrer, and a Dean-Stark trap is charged with 300 parts xylene, 5 parts of poly(propylene oxide) with a number average molecular weight of 4000 atomic mass units, and 3 parts lauroyl sarcosine (Hamposyl L). The mixture is refluxed by heating to 140°–145° C. until 0.8 equivalents of water are collected. The solvent is removed by ambient pressure distillation and a yellow semi-solid collected. The absences of infrared aliphatic O-H bending absorption at 3444 cm$-1$, aliphatic COO-H bending at 3481 cm$-1$, and aliphatic acid (C=O stretching absorbance at 1731 cm$-1$ confirms the successful chemical transformation.

EXAMPLE 2

Preparation of Poly(propylene oxide)-di(cocoyl sarcosinate)

Cocoyl sarcosine (Hamposyl C) may be substituted for the lauroyl sarcosine (Hamposyl L) used in Example 1 and the procedure thereof used in this example.

EXAMPLE 3

Preparation of Poly(propylene oxide)-di-(Tallowoyl sarcosinate)

Tallowoyl sarcosine (Hamposyl T) may be substituted for the lauroyl sarcosine (Hamposyl L) used in Example 1 and the procedure thereof used in this example.

EXAMPLE 4

Preparation of Poly(propylene oxide)-di(Stearoyl sarcosinate)

Stearoyl sarcosine (Hamposyl S) may be substituted for the lauroyl sarcosine (Hampsoyl L) in Example 1 and the procedure thereof used in this example.

The lubricating oil compositions of the present invention may be made by any procedure for making lubricating oil compositions. Typically, the additive is added to the lubricant by simply mixing the components together, producing a lubricant with increased oxidation and corrosion resistance.

The lubricating oil component of the lubricating oil compositions can typically include one or any combination of the following: hydrocarbon oils, such as those having naphthenic base, paraffinic base, mixed base mineral oils; oils derived from coal products; synthetic oils, such as alkylene polymers including polypropylene and polyisobutylene having molecular weights of between about 250 and 2500; and the like. The type of lubricant can vary depending upon the particular application or properties desired. For example, marine diesel engine lubricants can contain hydrocarbon lubricating oil having a Total Base Number (TBN) of 3–8, typically 6, which may be made by blending paraffinic Solvent Neutral Oil (SNO)—20 having a Viscosity Index (VI) of about 92 and a viscosity of 47–53 centistokes (Cst.) at 40° C. and of 6.65–7.15 CSt. at 100° C., with a paraffinic SNO—50 having a VI of about 93 and a viscosity of 158–180 CSt at 40° C. and of 15.3–16.4 at 100° C. Typical railway diesel engine lubricants can contain mixtures of paraffinic mineral oil having a viscosity of 5.5–10.0, such as 8.5 CSt at 100° C., paraffinic mineral oil having a viscosity of 8.0–15.0, such as 14.5 CSt at 100° C., and naphthenic pale oil having a viscosity of 8.0–15.0, such as 14.2 CSt at 100° C. Preferred lubricants include: N300 Pale Oil from Texaco Inc.; N900 Pale Oil from Texaco Inc.; and the like.

The present additive may be added to the base lubricating oil in any minor, effective, rust and haze inhibiting amounts. Preferably the additive will be added to the base lubricating oil in amounts of about 0.1 to about 5 wt. % based on the weight of the lubricating oil. More preferably the effective amount is about 1 wt. % to about 3 wt. %, based upon the weight of the lubricating oil. The additive mixture may be added separately, or as a component of an additive package which contains other additives.

The lubricant composition can contain, if desired, any other materials useful in lubricants. Such other materials include, among others, one or more of the following: dispersants; detergents; viscosity index improvers; antifoamants; anti-wear agents; demulsifiers; other anti-oxidants; other corrosion inhibitors; and other materials useful in lubricants. Preferred optional additives or additive packages include: ORONITE ® 2939 from Chevron Chemical Company;

Polymethylmethacrylate, a pour point depressant is manufactured and sold by Rohm Haas of Philadelphia, PA. The amount of such materials may be any desired amounts which provide the desired properties.

The additive of the present invention is advantageous in that it imparts rust inhibition to diesel lubricating oil compositions without causing haze to form. These advantages are illustrated by the comparison of the Reference Examples 1, 2, 3 and 4 listed below in Table I. Example A is commercially available Doro AR®, a slow speed marine crankcase formulation available from Deutsche Texaco Additive. Example B is the same lubricant, Doro AR®, with the commercial rust inhibitor, Surfonic N-60 ™, removed. Example C is Doro AR® with the commercial rust inhibitor removed and the additive of Example 4 substituted in its place.

TABLE 1

| Material | Reference | Example 1 | Example 2 | Example 3 | Example 4 |
|---|---|---|---|---|---|
| SNO-20G DTA | 39.30 | 39.30 | 39.30 | 39.30 | 39.30 |
| SNO-50 DTA | 55.80 | 56.15 | 55.15 | 55.15 | 55.15 |
| detergent[1] | 3.60 | 3.60 | 3.60 | 3.60 | 3.60 |
| anti-wear agent[4] | 0.65 | 0.65 | 0.65 | 0.65 | 0.65 |
| anti-oxidant[2] | 0.30 | 0.30 | 0.30 | 0.30 | 0.30 |
| anti-foam agent[5] (ppm) | 150 | 150 | 150 | 1.50 | 1.50 |
| anti-rust agent[3] | 0.35 | — | — | — | — |
| Experimental Additive | — | 1.00 | 1.00 | 1.00 | 1.00 |

[1] Oronite 218A brand of overbased sulfurized calcium alkylphenolate having a TBN of 147, available from the Chevron Oil Company.
[2] Vanlube NA brand of dinonyl phenyl amine, available from RT Vanderbilt, of Norwalk, Ct.
[3] Surfonic N-60, available from the Texaco Chemical Company, Houston, Texas.
[4] Zinc di-thiophosphate
[5] TX-1416 brand of anti-foam agent, available from the Texaco Chemical Company.

The lubricating oil compositions of both the Reference and Examples 1, 2, 3 and 4 were subjected to the ASTM D-665 Saltwater Test to determine the level of rust inhibition.

ASTM D-655 Saltwater Test

This test method was used to evaluate the ability of inhibited mineral oils to aid in preventing the rusting of ferrous parts should water become mixed with the oil.

A mixture of 300 ml of the oil under test is stirred with 30 ml of synthetic sea water as required, at a temperature of 60° C. (140° F.) with a cylindrical steel specimen completely immersed therein. The test is run for 24 hours. The specimen is observed for signs of rusting and, if desired, the degree of rusting.

In addition, each composition was tested with the Hazitron ™, an instrument which measures haze.

Hazitron test Method

This method is intended for the determination of the clarity of petroleum products such as lubricating oils and their additives. The Hazitron instrument rates clarity essentially as perceived by the human eye.

The Hazitron measures light scattering caused by haze. The method is based on measurements of transmitted light through the sample placed in two positions of the sample compartment.

Clarity is an important characteristic of lubricating oils and their additives. A method using the Hazitron allows one to evaluate clarity objectively.

Hazitron values of 15 or less indicate commercially acceptable product clarity.

The results of the ASTM D-665 Saltwater Test and the Hazitron test are summarized below in Table II.

TABLE II

| Material | Reference | Example 1 | Example 2 | Example 3 | Example 4 |
|---|---|---|---|---|---|
| Hazitron Turbidity | 55 (Fail) | 9 (Pass) | 8 (Pass) | 11 (Pass) | 6 (Pass) |
| ASTM Salt Water Test | Pass | Pass | Pass | Pass | Pass |

The results of these test clearly show that the additive of the present invention provides marine crankcase lubricants with rust inhibition which is at least as effective as the commercially used rust inhibitor. In addition, it is also clear that the commercial rust inhibitor causes haze to form in the lubricant while the additive of the present invention is haze free in the lubricating oil composition.

Thus, the additive of the present invention effectively imparts haze free rust inhibition to lubricating oil compositions.

We claim:

1. A lubricating oil additive which comprises the reaction product of (a) an alkyl sarcosine represented by the formula

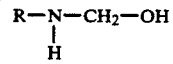

where R is a ($C_3$–$C_{30}$) alkyl radical; and (b) a poly(propylene oxide) represented by the formula

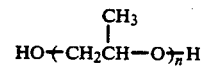

where n varies from 1 to 5000.

2. The lubricating oil additive of claim 1 where R is an alkyl radical containing about 10 to about 30 carbon atoms.

3. The lubricating oil additive of claim 1 where about 2 moles of the alkyl sarcosine is reacted with about 1 mole of the poly(propylene oxide).

4. A lubricating oil composition comprising a major portion of a base hydrocarbon lubricating oil and a minor portion, sufficient to impart rust and haze inhibition to the lubricating oil composition, of a lubricating oil additive comprising the reaction product of:

(a) an alkyl sarcosine represented by the formula

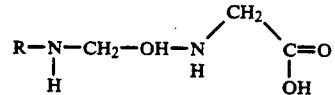

where R is a ($C_3$–$C_{30}$) alkyl radical optionally containing one or more heteroatoms; and (b) a poly(propylene oxide) represented by the formula

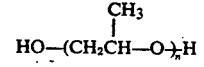

where n varies from 1 to 5000.

5. The lubricating oil composition of claim 4 where R is a lauroyl group.

6. The lubricating oil composition of claim 4 where R is a cocoyl group.

7. The lubricating oil composition of claim 4 where R is a tallowoyl group.

8. The lubricating oil composition of claim 4 where R is a stearoyl group.

9. The lubricating oil composition of 4 where the repeat unit n in poly(propylene oxide) is 200.

* * * * *